(12) United States Patent
Wang et al.

(10) Patent No.: US 6,566,122 B1
(45) Date of Patent: May 20, 2003

(54) **SUPER-SECRETING *SACCHAROMYCES CEREVISIAE* STRAINS**

(75) Inventors: Bi-Dar Wang, Taipei (TW); Dz-Chi Chen, Taipei (TW); Tsong-Teh Kuo, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/596,292

(22) Filed: Jun. 16, 2000

(51) Int. Cl.$^7$ .............. C12N 1/14; C12N 1/16; C12N 1/18; C12N 9/24; C12N 15/00; C12N 9/00

(52) U.S. Cl. .............. 435/254.21; 435/183; 435/200; 435/252.3; 435/243; 435/320.1

(58) Field of Search ................ 435/440, 471, 435/252.3, 254.2, 320.1, 69.1, 183, 200, 252–3, 254.21, 243

(56) References Cited

U.S. PATENT DOCUMENTS

| | | | |
|---|---|---|---|
| 5,312,735 A | 5/1994 | Fink et al. | 435/69.1 |
| 5,705,616 A | 1/1998 | Lehle et al. | 530/395 |
| 5,798,226 A | 8/1998 | Lehle et al. | 435/69.1 |
| 6,210,954 B1 * | 4/2001 | Kuo et al. | 435/254.2 |

OTHER PUBLICATIONS

Turner et al. 1991, Optimization of uro–kinase secretion from recombinant S.cerevisiae. Biotechnol. Bioeng. vol. 37:869–875.*

Chen et al., "A Variant of Saccharomyces cerevisiae pep4 Strain With Improved Oligotrophic Proliferation, Cell Survival and Heterologous Secretion of α–amylase", Appl Microbiol Biotechnol 51:185–192, 1999.

Sakai et al., Enhanced Secretion of Human Nerve Growth Factor From Saccharomyces Cerevisiae Using an Advanced δ–Integration System, Bio/Technology 9:1382–1385, 1991.

Sakai et al., "Isolation and Characterization of Mutants Which Show an Oversecretion Phenotype in Saccharomyces Cerevisiae", Genetics 119:499–506, 1988.

Smith et al., "Heterologous Protein Secretion from Yeast", Science 229:1219–1224, 1985.

Suzuki et al., "Yeast Mutants with Enhanced Ability to Secrete Human Lysozyme: Isolation and Indentification of a Protease–deficient Mutant", MGG 58–63, 1989.

* cited by examiner

Primary Examiner—Rebecca E. Prouty
Assistant Examiner—Manjunath N. Rao
(74) Attorney, Agent, or Firm—Fish & Richardson P.C.

(57) ABSTRACT

A super-secreting protease A-deficient strain of *Saccharomyces cerevisiae*, which, when starved for a nitrogen source, undergoes a pseudohyphal-like growth mode, and, when transformed with a secretion vector containing a DNA sequence which encodes a mouse α-amylase, is capable of secreting the mouse α-amylase at 2,000 to 15,000 units/liter.

21 Claims, No Drawings

SUPER-SECRETING SACCHAROMYCES CEREVISIAE STRAINS

BACKGROUND

Yeast species can be used as hosts for the production of heterologous proteins. As unicellular microorganisms, yeasts share the advantages of bacterial systems with regard to ease of manipulation and growth. Yet, unlike bacteria, yeast cells possess an eukaryotic subcellular organization that is capable of accurate posttranslational processing and modification of many mammalian proteins.

The yeast *Saccharomyces cerevisiae* has been used extensively for the production of many heterologous proteins, given that host-vector systems, genetic information, and recombinant DNA techniques are well established for this organism. In addition, industrial-scale production of heterologous proteins by yeast benefits from an established fermentation technology.

Protease A-deficient strains of *S. cerevisiae* are commonly used as host cells because of the associated decrease in protein hydrolysis; however, these strains exhibit a reduced proliferative capacity. A recently isolated protease A-deficient strain having enhanced ability to secrete heterologous protein showed a higher viability and mitotic capacity, as compared with the parental and wild-type strains. Chen et al., *Appl Microbiol Biotechnol* 51:185–192, 1999.

The PMR1 gene encodes a $Ca^{2+}$-dependent ATPase in *S. cerevisiae*. According to earlier reports, pmr1 mutants exhibited a 5- to 50-fold increase in the abundance of secreted prochymosin, bovine growth hormone, or scuPA. Smith et al., *Science* 229:219–1224, 1985; Turner et al., *Biotechnol Bioeng* 37:869–875, 1991.

SUMMARY OF THE INVENTION

This invention relates to a super-secreting protease A-deficient strain of *Saccharoinyces cerevisiae*, which, when starved for a nitrogen source, undergoes a pseudohyphal-like growth mode, and, when transformed with a secretion vector containing a DNA sequence that encodes a mouse a-amylase (e.g., pMS12; see below for details), is capable of secreting the mouse a-amylase at 2,000 to 15,000 units/liter (e.g., 3,000 to 14,000, 6,000 to 13,000, or 9,000 to 12,000 units/liter). The strain of this invention further has one or more of the characteristics of reduced glycosylation of the mouse a-amylase, high stability of the vector, inability to grow at 37° C., and cell cycle-dependent secretion of the mouse a-amylase. It can be either a PMR1-positive strain (e.g., NI-C-D4) or a pmr1-deficient strain (e.g., DP-1). Deposit of the strain NI-C-D4 was made on Mar. 13, 2000 and deposit of the strain DP-1 was made on Jun. 22, 2000, both with the Culture Collection Research Center, Hsinchu, Taiwan, where the deposits were given Accession Number CCRC 920020 and Accession Number CCRC 920021, respectively.

Set forth below is a process for preparing a strain of the present invention: (1) transforming cells of a protease A-deficient and PMR1 positive *S. cerevisiae* parent strain with a secretion vector that expresses and secrets a heterologous protein, e.g., hepatitis surface antigen HBsAg, which inhibits the growth of the transformed cells; (2) cultivating the transformed cells in a medium containing a reduced nitrogen source and selecting a non-inhibited mutant strain, the non-inhibited mutant strain having unstable phenotypes; (3) maintaining cells of the unstable non-inhibited mutant strain in the stationary phase for an extended period of time and choosing a stable non-inhibited mutant strain; (4) growing cells of the stable non-inhibited mutant strain under conditions which favor the curing of the secretion vector; (5) crossing the vector-cured strain with a protease A-positive strain of *S. cerevisiae* (PMR1-positive or pmr1-deficient) to acquire heterozygotes; (6) allowing the heterozygotes to sporulate to produce haploid segregants; and (7) screening the segregants to select a strain of *S. cerevisiae* which has a higher secretion capability than the parent strain. Before crossing a PMR1-positive vector-cured strain with a protease A-positive strain, both strains may be transformed with a vector encoding a marker secretion protein. In any event, if the vector-cured strain is crossed with a protease A-positive and PMR1-positive strain, the PMR1 gene of the selected super-secreting strain can be disrupted to produce a strain with an even higher secretion capability.

For the sole purpose of describing a characteristic of the strains of this invention, the capability of each strain to secrete a heterologous protein is based on the amount of a mouse α-amylase in the supernatant from a 4-day culture of a pMS12-transformed strain determined by the procedure described in the actual examples below. Thus, it will be understood that the above-described strains can be used to produce various valuable heterologous proteins, such as HbsAg or human GM-CSF (granulocytelmacrophage colony-stimulating factor. Similarly, mouse α-amylase is also used to demonstrate reduced glycosylation of the secreted protein (i.e., as compared with wild-type strains) and cell cycle dependent secretion, and pMS12 is used to demonstrate high stability of the vector (i.e., >50% of cells exhibiting amylolytic activity at 96 h). Again see the actual examples below for the detailed procedures.

The details of one or more embodiments of the invention are set forth in the decription below. Other features, objects, and advantages of the invention will be apparent from the description and from the claims.

DETAILED DESCRIPTION OF THE INVENTION

A method of producing a strain of the present invention includes the steps of crossing an oligotrophic protease A-deficient *S. cerevisiae* (e.g., strain NI-C described in Chen et al., 1999 and U.S. patent application Ser. No. 09/182,377) or its equivalent strain with a wild-type strain to obtain heterozygous diploid cells, inducing the diploid cells to form spores or haploid segregants, and then screening the segregants for a super-secreting strain of this invention (e.g., by a halo assay in which mouse α-amylase is used as a marker protein).

Without further elaboration, it is believed that the above description has adequately enabled the present invention. The following specific examples are, therefore, to be construed as merely illustrative, and not limitative of the remainder of the disclosure in any way whatsoever. All of the publications cited herein are hereby incorporated by reference in their entirety.

MATERIALS AND METHODS

*S. cerevisiae* strains NI-C, Sey6211, NI-C-D4, TL154, and W303 served as expression hosts (Table 1). NI-C (Chen et al., 1999) and NI-C-D4 are protease A-deficient strains, and Sey6211, TL154, and W303 are wild-type strains. Other strains used in this study are listed in Table 1:

TABLE 1

Genotypes of S. cerevisiae strains used in this study.

| Strain | Genotype |
| --- | --- |
| NI-C | α, trp1, pep4 |
| Sey6211 | α, ade2-1, his3, trp1, ura3-52 |
| NI-C-D4 | α, trp1, ura3, pep4 |
| TL154 | α, trp1, leu2 |
| W303 | α/α, trp1/trp1, leu2/leu2, ura3/ura3, his3/his3, ade2/ade2 |
| A4509 | α, trp1, pep4::LEU2, leu2 |
| Dy150 | α, trp1, leu2, ura3, his3, ade2, can1 |
| C30 | α, trp1, leu2, pep4 |
| BJ2168 | α, prb1-1122, prc1-407, pep4-3, trp1, leu2, ura3-5 |
| SP1 | α, pmr1::KAN$^r$, ade2-1, his3, trp1, ura3-52 |
| DP1 | α, pmr1::KAN$^r$, trp1, ura3, pep4 |

Plasmid pMS12 (Kim et al., Appl Environ Microbiol 54:966–971,1988) was derived from pMA56 (Valenzuela et al., Nature 298:555–557, 1982) and contained the mouse salivary α-amylase cDNA. The α-amylase cDNA, including the sequence encoding the 15-amino acid signal peptide, was inserted by means of an EcoRI linker downstream of position –14 of the ADH1 gene. The expression vector also contained the *Escherichia coli* origin of replication and the β-lactamase gene of pBR322, a segment of yeast 2-$\mu$m DNA containing an origin of replication, and the yeast TRP1 gene.

Yeast strains were grown in the following media (all percentages are w/v): YPD (1% yeast extract, 2% peptone, 2% glucose), YNBD (0.17% yeast nitrogen without amino acids and ammonium sulfate, 0.5% ammonium sulfate, 2% glucose), YPDS agar (1% yeast extract, 2% peptone, 2% glucose, 2% soluble starch, 2% agar), ASNS agar (0.17% yeast nitrogen without amino acids and ammonium sulfate, 0.5% asparagine, 2% starch, 2% agar), and ASNDS agar (ASNS agar supplemented with 2% glucose). Amino acids and nucleotides were added to satisfy auxotrophic requirements in all experiments. For ascospore formation, diploid cells harvested from YPD were resuspended in 1% potassium, acetate and sporulated for 5–7 days at 23° C.

Yeast cells were harvested from YPD cultured in the stationary phase at a density of ~2.5×10$^8$ cells/ml. Transformation was performed,as described in Chen et al., *Curr Genet* 3–84, 1992.

Transformed strains were cultivated on YNBD agar for 2 to 3 days for selection. Cells were transferred to YPDS agar for screening of transformants that show a high level of α-amylase secretion, which was evident from the formation of a halo (reflecting starch degradation) around the colonies. For determination of growth curves, transformants grown in YNBD were transferred to YPD broth at a density of 1×10$^6$ cells/ml and cultured for 4 days in a rotary shaker at 125 rpm and 28° C.; cell number at various times was quantified by direct counting with a hemocytometer.

Measurement of Intracellular and Extracellular α-amylase Activity

Cells cultivated in YPD broth at an initial density of 1×10$^6$ cells/ml were harvested at various times by centrifugation (4000×g, 5 min, 4° C.). The pellet was used to prepare a cell extract, 20 $\mu$l of which were assayed for determination of intracellular amylase activity. The supernatant was buffered with 15 mM Hepes-NaOH (pH 7.0), and 20 $\mu$l of the resulting medium was assayed for determination of the secreted, extracellular amylase activity. Both intracellular and extracellular activities were assayed with an α-amylase diagnostic kit (Sigma).

Preparation of Cell Extract

Cells grown in YPD medium were resuspended and washed by centrifugation, and the new pellet was buffered with Hepes and agitated with chilled, acid-washed glass beads (diameter, 0.45 mm) as described in Dunn et al., Preparation of protein extract from yeast. In *Current Protocols in Molecular Biology*, vol. 2, Ausubel et al., (eds). Wiley Interscience: New York; 13.13.4–13.13.5, 1996. After centrifugation to remove the beads, the resulting supernatant was collected as the crude cell extract. For long-term storage, crude cell extracts were divided among small tubes, rapidly frozen in liquid nitrogen, and stored at –80° C.

APE Test

Replica strains to thick YPD plate (40–45 ml/100-mm plate) and grown for 3 days at 30° C. To form the overlay mix, 2.5 ml of the ester solution (N-acetyl-DL-phenylalanine β-naphthyl ester: in a solution of 1 mg/ml dimethylformamide) was added to 4 ml of molten agar (0.6% agar, molten, held at 50° C.) in a 13×100 mm tube. The solution was vortexed until the schieren pattern disappeared. After the bubbles exited, the content was poured over the surface of colonies. After 10 min, the surface of the agar was carefully flooded with 4.5–5 ml of a solution of Fast Ganet GBC (prepared freshly, 5 mg/ml 0.1M Tris-HCl, pH7.3–7.5). The agar was allowed to stand for 5–10 min at room temperature. By APE test, wild-type colonies turn red in color, while mutants like prc1 (Wolf, et al., *J. Bacteriol.* 123:1150–1156, 1975) remain white or turn pink.

Endoglycosidase H (Endo H) Treatment and Immunoblot Analysis of (α-amylase

For immunoblot analysis, stationary-phase cultures were diluted 1:100 and grown in YPD medium. At various times, cells were removed by centrifugation, and the remaining supernatant was collected and its protein concentration measured by the modified Lowry method. Equivalent amounts of supernatant protein were boiled for 10 min in Endo H denaturing buffer, after which each sample was split and half was incubated overnight at 37° C. with 1000 U of Endo H (BioLab). The treated and untreated samples were then fractionated by SDS-polyacrylamide gel electrophoresis (PAGE) on a 4 to 12% gradient gel, and the separated proteins were transferred electrophoretically to a polyvinylidene difluoride membrane for 2 h at 30 V. The membrane was then incubated with rabbit antibodies to human α-amylase (Sigma) at a dilution of 1:1000. After washing in TTBS buffer [20 mM Tris-HCl (pH 8.0), 150 mM NaCl, 0.05% Tween 20], the membrane was incubated with alkaline phosphatase-conjugated goat antibodies to rabbit immunoglobulin G (Bio-Rad). The membrane was washed again, and immune complexes were detected by enhanced chemiluminescence.

Cell Cycle Synchronization and Immunoblot Analysis of CDC28 and CLB2

Yeast cells were arrested in G$_1$ phase of the cell cycle by growth to stationary phase in YPD medium, and small G$_1$ cells were isolated by elutriation. For immunoblot analysis of CDC28 and CLB2 proteins, cells were harvested by centrifugation, washed once with 10 mM Tris-HCl (pH 7.5), and resuspended in 200 $\mu$l of lysis buffer [50 mM Tris-HCl (pH 7.5), 1 mM EDTA, 50 mM dithiothreitol, 1 mM phenylmethylsulfonyl fluoride, 500 mM TPCK, 25 $\mu$M TLMK, pepstatin A (2 $\mu$g/ml)]. After addition of an equal volume of glass beads, the cells were broken by vigorous vortex-mixing for 3 min at 4° C. The glass beads and cell debris were removed by centrifugation, and equivalent amounts of the remaining cell extract (50 $\mu$g of total protein)

were fractionated by SDS-PAGE on a 10% gel. The separated proteins were transferred to a polyvinylidene difluoride membrane as described above, and the membrane was then incubated with monoclonal antibodies to CLB2 (1:300 dilution) (Calbiochem) or to CDC28 (1:500 dilution) (Calbiochem). Immune complexes were detected with alkaline phosphatase-conjugated secondary antibodies and enhanced chemiluminescence.

RESULTS

Screening for α-amylase-oversecreting Mutants

A halo assay was used to identify mutant yeast strains with a supersecretion phenotype. The test relied on the detection of the clear halo zones that form around yeast cells that secrete α-amylase when the cells are cultured on YPDS plates. Chen et at. 1999; and Chen, et al., J Biotechnol 29:329–334, 1993. The sizes of such clear regions are related to the amount of α-amylase secreted by each colony.

Several HBsAg-induced mutants with different phenotypes were previously isolated Chen et al., Curr Genet 27:201–206, 1995. Among them, NI-C was isolated and characterized as an oligotrophic variant of an HiBsAg-resistant proteinase A-deficient strain with improved secretion of mouse α-amylase (Chen et al., 1999). To further characterize the mutation responsible for the enhanced secretion ability of NI-C, NI-C was used as the α-type parent strain for mating with wild-type strains to derive segregants that exhibit the enhanced secretory capacity. The heterozygous diploid NI-C/Sey6211, which exhibited a highest sporulation frequency, was chosen for further isolation of the super-secreting segregants. By random spore isolation, 400 of the resulting haploid segregants obtained from the pMS12-transformed diploid NI-C/Sey6211 cells were screened for their ability to secrete α-amylase on YPDS agar. After incubation for 3 days at 28° C., 42 haploid colonies were observed to formn larger halos than did the transformed NI-C parent. The segregant that formed the largest halo, NI-C-D4, was characterized further as a super-secreting mutant; the APE test ealed that this mutant was a protease-A deficient strain. The NI-C-D4 mutant, screened for at 28° C., was not able to grow at 37° C.

The secretory efficiency of the NI-C-D4 mutant harboring pMS12 (pMA56, vector only, used as a negative control) was further compared with those of the transformed parental NI-C and Sey6211 strains, and with those of the transformed wild-type haploid TL154 and diploid W303, with the use of the halo assay. More specifically, the resulting transformants were examined for their ability to secrete α-amylase on the basis of halo formation on YPDS plates. The transformants were patched at an initial density of $1 \times 10^6$ cells per colony and were cultured at 28° C. The transformed NI-C-D4 cells rapidly secreted α-amylase into medium and the resulting clear halo was observed within 4 hours. The size of the resulting clear zone observed with NI-C-D4 was greater than those with the other strains. This result suggested that the secretion capacity of heterologous α-amylase was increased in the NI-C-D4 mutant strain.

Growth and α-amylase Secretion

All tested strains were transformed with the mouse α-amylase secretion vector pMS12, and transforrnants were selected in minimal medium before transfer to and culture in nonselective YPD medium at an initial density of $1 \times 10^6$ cells/ml at 28° C. for 96 h. Similar growth curves were observed for all of the transformed yeast strains NI-C-D4, NI-C, Sey6211, TL154 and W303. Like NI-C, NI-C-D4 underwent a pseudohyphal-like growth mode when starved for a nitrogen source. The super-secreting mutant NI-C-D4, its parental strains NI-C and Sey6211, and the wild-type strains TL154 and W303 secreted α-amylase into the culture medium in a manner that appeared related to cell growth. That is, the amount of α-amylase activity in the culture medium increased during the log phase of growth and reached a plateau during stationary phase. After cultivation for 96 h, the amounts of α-amylase activity in the culture supernatants of transformed strains NI-C, Sey6211, and NI-C-D4 were 1580, 354, and 4143 units/liter, respectively. In several experiments, the amount of α-amylase secreted by the NI-C-D4 mutant was 12 to 13 times that for the parental wild-type strain Sey6211 and 7- to 10-fold greater than that secreted by haploid TL154 and diploid W303 wild-type strains. The secretion capacity of the NI-C-D4 can be further improved (up to 15,000 units/L) by substituting PKG1 (or GAP1), promoter for ADH1 promoter of the secretion vector and increasing the cell density of YPD culture to $10^9$ cells/ml.

Viability and Stability of Transformed Yeast Strains

To investigate the mechanism responsible for the increased efficiency of heterologous protein secretion in strain NI-C-D4, the viability and stability of transformed yeast strains were compared. After culture for 96 h in YPD medium, the viability of transformed NI-C-D4 cells was only 33 to 72% of that of the parental (NI-C and Sey6211) and wild-type (TL154 and W303) strains. Plasmid stability, the number of amylolytic cells expressed as a percentage of the number of plated cells at 96 h, was determined following the procedures described in Chen et al., 1993. More specifically, the stability of the five yeast strains transformed with pMS12 was assessed based on the percentage of cells possessing amylolytic activity on YPDS plates after culture for various times in YPD medium (in the absence of selection pressure). The stability of transformed NI-C-D4 cells was markedly greater (50–60% of cells exhibited amylolytic activity at 96 h) than that of the parental NI-C and Sey6211 transformants as well as that of the other wild-type transformants. Thus, the high stability of transformed NI-C-D4 cells likely contributes to the high level of secretion of α-amylase by this strain.

Immunoblot Analysis of Intracellular and Secreted α-amylase

The secretion of mouse α-amylase by transformed NI-C, Sey6211, and NI-C-D4 cells was confirmed by immunoblot analysis. More specifically, transformed strains NI-C, Sey6211, and NI-C-D4 were cultured at an initial density of $1 \times 10^6$ cells/ml in YPD medium for 4 days, after which 1.5-ml samples of culture supernatant were harvested. Proteins in these samples were precipitated with ammonium sulfate, boiled, and then subjected to immunoblot analysis with antibodies to α-amylase. Also, cells were harvested from 1.5-ml samples of 96-h cultures as just described, and extracts were prepared. The extract proteins were then subjected to immunoblot analysis with antibodies to α-amylase. Immunoblot analysis of cell extracts of the three transformed strains with antibodies to α-amylase revealed a prominent immunoreactive protein of 53 kDa. The YPD culture supernatants of the three strains yielded two well-defined immunoreactive proteins of 53 and 55 kDa. Immunoblot analysis also showed that both the extracellular and intracellular amounts of α-amylase produced by the mutant NI-C-D4 were markedly greater than those produced by the parent strains. The bands corresponding to α-amylase secreted from NI-C-D4 transforinants migrated faster on electrophoresis than did those corresponding to α-amylase secreted by Sey6211 transformants, because of differences in glycosylation state of secreted α-amylase between the two strains.

The glycosylation state of the secreted α-amylase from yeast transformants was further investigated. More specifically, transforned strains TL154, NI-C, and NI-C-D4 were cultured in YPD medium until stationary phase, after which equal amounts of protein (~30 μg) from culture supernatants were treated or not treated with Endo H, which cleaves N-linked oligosaccharide chains from glycoproteins. The samples were then subjected to immunoblot analysis with antibodies to α-amylase. Whereas untreated culture supernatants of transformed TL154, NI-C, and NI-C-D4 cells contained immunoreactive proteins of 53 kDa (major) and 55 kDa (minor), equivalent amounts of culture supernatants treated with Endo H showed only the 53-kDa protein. These results indicate that the 55-kDa protein is the mature glycosylated form of α-amylase, whereas the 53-kDa band corresponds to the unglycosylated, cytoplasmic form of the enzyme. It has been known that the 53-kDa protein is responsible for most of the activity of secreted mouse α-amylase. Chen et al., *Yeast*, 16:207–217, 2000. Thus, it is possible that the increased amount of the 53-kDa protein and the increased ratio of the 53-kDa protein to the 55-kDa protein in the supernatant of NI-C-D4 transformants contribute to the associated increase in secreted α-amylase activity.

Reduced Proteolysis of α-amylase Secreted by NI-C-D4 was Caused by Protease A Deficiency Undesirable proteolytic processing of heterologous proteins produced in yeast has been described (Romanos et al., *Yeast* 8:423–488,1992). In a manner analogous to that described above, strains NI-C, Sey6211, NI-C-D4, and TL154 harboring pMS12 were cultured in YPD medium for 200 h, after which 1.5-ml samples of culture supernatant were collected and subjected to immunoblot. Degradation products were more prominent in the supernatants of 200-h cultures of transformed Sey6211 and TL154 cells than they were in the corresponding culture supernatants of transformed protease A-deficient mutants NI-C and NI-C-D4. The data indicates that protease A deficilency is responsible for the reduced α-amylase degradation in transformed NI-C and NI-C-D4 mutants.

Genetic Analysis of the Mutant NI-C-D4

In an attempt to characterize the genetic mutation (or mutations) responsible for the super-secretion phenotype of strain NI-C-D4, this strain was backcrossed to the wild-type strain Dy150, the protease-deficient strains BJ2168 and C30, and the parental strain Sey6211. The resulting Ade+, His+, Leu+ diploid strains were cultivated on ASNS agar supplemented with uracil, and their ability to form halos was assessed. After incubation for 2 days at 28° C., all diploids had formed halos that were smaller than that formed by transformed NI-C-D4, indicating that the mutation is recessive.

Mutation of Super-secretion was Independent of Protease A Deficiency

To investigate the relationship of the protease deficiency to the super-secretion, meiotic segregants, obtained by micromanipulating the spores of diploids from cross between the pMS12-transformed Sey6211 and pMS12-transformed NI-C-D4 mutants, were inoculated on a YPS agar plate for 3 days. The halos were observed around all the segregants. In other words, the super-secretion phenotype was observed in two segregants of each tetrad. This result indicates that a single chromosome mutation caused the super-secretion of α-amylase. The mutation is referred to as ssa1.

The protease deficiency was examined by APE test in respective segregants. Protease A is a key enzyme for maturation of proproteinase B and proCPY. Jones et al., *Genetics*102:665–677, 1982. As mentioned above, protease A deficiency results in a reduced proteolysis of the super-secreting mutant NI-C-D4. Therefore, it was expected that the super-secretion was caused by mutation in the protease A gene, i.e., the PEP4 gene. Segregants of six tetrads were screened for α-amylase secretion. Table 2 shows amylase production and protease activity in each of four respective tetrads. These data also show that the two genes (ssa1 and pep4) segregated independently into spores from the diploid. Protease defective segregants from the diploid did not always form large halo, indicating that the protease A deficiency per se is not the sole cause of the super-secretion. The segregation data for the two genes was 2PD, 2NPD, 2TT (Table 2), from which the distance between ssa1 and pep4 was calculated to be 21.4 cM based on the formula of Perkins, *Genetics* 34: 607–626, 1949.

TABLE 2

Segregation of α-amylase supersecretion and protease deficiency

| Segregant | Halo assay | amylase activity (U/liter) | APE test | Expected genotype |
|---|---|---|---|---|
| a1 | S | nd[a] | Pink | SSA1 pep4 |
| a2 | S | nd | Red | SSA1 PEP4 |
| a3 | L | 1891 | Red | ssa1 PEP4 |
| a4 | L | 1681 | Pink | ssa1 pep4 |
| b1 | L | 2109 | Red | ssa1 PEP4 |
| b2 | L | 1037 | Red | ssa1 PEP4 |
| b3 | S | 28 | Pink | SSA1 pep4 |
| b4 | S | 70 | Pink | SSA1 pep4 |
| c1 | S | 21 | Red | SSA1 PEP4 |
| c2 | L | 953 | Pink | ssa1 pep4 |
| c3 | S | 35 | Red | SSA1 PEP4 |
| c4 | L | 628 | Pink | ssa1 pep4 |
| d1 | L | 635 | Red | ssa1 PEP4 |
| d2 | S | nd | Red | SSA1 PEP4 |
| d3 | L | 685 | Pink | ssa1 pep4 |
| d4 | S | nd | Pink | SSA1 pep4 |
| e1 | L | 825 | Red | ssa1 PEP4 |
| e2 | L | 690 | Red | ssa1 PEP4 |
| e3 | S | 92 | Pink | SSA1 pep4 |
| e4 | S | 98 | Pink | SSA1 pep4 |
| f1 | L | 750 | Pink | ssa1 pep4 |
| f2 | L | 1350 | Pink | ssa1 pep4 |
| f3 | S | 28 | Red | SSA1 PEP4 |
| f4 | S | 28 | Red | SSA1 PEP4 |

[a]nd, not detected; L, large halo formation on a YPS agar plate; S, small halo formation. The APE test to identify protease deficiency was performed using patches of colonies incubated for 2 days on YPD agar plates. Culture supernatant was collected after 4 days cultivation in ASND medium supplemented with amino acids at 28° C. and was used to measure the α-amylase activity. Segregants designated by the same number were from the same ascus.

Mutation of Super-secretion Affected Glycosylation

Results discussed above have revealed that the secreted α-amylase by pMS12transformed NI-C-D4 mutant was lower glycosylated than those by transformed wild-type strains. To further elucidate the relationship between ssa1 and the mutation responsible for the defective glycosylation, the resulting meiotic segregants were analyzed for their secretion abilities and glycosylation states. As shown in Table 3, these two phenotypes cosegregated in all 24 asci tested. These data suggest that a single mutation causes both supersecretion and lower-glycosylation.

TABLE 3

Cosegregation of supersecretion and low-glycosylation mutation

| Halo assay | APE test | Glycosylation state[a] |
|---|---|---|
| S | Pink | high |
| S | Red | high |
| L | Red | low |
| L | Pink | low |
| L | Red | low |
| L | Red | low |
| S | Pink | high |
| S | Pink | high |
| S | Red | high |
| L | Pink | low |
| L | Red | low |
| S | Pink | high |
| S | Red | high |
| L | Red | low |
| L | Pink | low |
| S | Pink | high |

[a]high, high-glycosylation state of secreted α-amylase; low, low-glycosylation state of secreted α-amylase from the segregants.
Diploid cells from the cross between pMS12-transformed NI-C-D4 and pMS12-transformed Sey6211 were caused to form spores. α-Amylase secretion and protease deficiency of resulting segregants were examined by the halo assay and APE test, respectively. The symbols are as for Table 2.

To characterize secreted α-amylase protein in the ssa1 mutant, immunoblot analysis was performed. More specifically, samples were withdrawn from supernatants of YPD cultures, boiled in the presence of SDS and a reducing agent, and subjected to SDS-PAGE for immunoblot analysis with antibodies to α-amylase. Transformed NI-C-D4 was shown to have a decreased amount of glycosylated α-amylase compared to wild-type cells. The same results were obtained with meiotic segregants from cross between NI-C-D4 and a wild-type strain. All segregants that were ssa1 mutants also had an antigen with lower glycosylation. These results suggest that the SSa1 gene is necessary for conversion of cytoplasmic protein to glycosylated protein in the secretory pathway.

Preparation of DPI a Protease-A Deficient and pmr1-deficient Strain

Since pmr1 mutants have been known to exhibit dramatic increase in the amount of secreted heterologous protein, it is possible that the PMR1 gene is a candidate for the SSA1gene. In order to elucidate the relationship between SSA1 and PMR1, a ssa1 pmr1 mutant DP1, derived by disruption of PMR1 gene in NI-C-D4, was constructed by PCR-based deletion method by transforming NI-C-D4 with the linearizing plasmid containing kanMX2-module marked pmr1 deletion. Baudin et al., Nucl. Acids Res. 21:3329–3330, 1993. Kan[R] transformants were selected and allele replacement was confirmed by colony PCR. A pmr1mutant SP1, derived by disruption of PMR1 genein Sey6211, was constructed in a similar manner. The secretion abilities of SP1 and DP1 were examined by the halo test on YPS plate. Both SP1 and DP1 mutants exhibited an improved secretion capacity than their parental strains Sey6211 and NI-C-D4, suggesting that ssa1 and pmr1 are two different mutations. Following the procedures set forth in the legend of Table 2 above, pMS12-transformed DP-1 secreted mouse α-amylase at 11,750 units/liter.

It has been suggested that the pmr1 cells are sensitive toward DTT, a drug known to induce accumulation of malfolded proteins in the, endoplasmic reticulum. Durr et al., Mol. Biol. Cell 9:1149–1162, 1998. The growth of ssa1 mutant in the presence of DTT was examined. While the pmr1 cells were found to be hypersensitive to DTT, the ssa1 mutant was not. The results thus indicate that the ssa1 mutation is distinct from the pmr1 mutation.

Cell Cycle Dependence of α-amylase Production by Transformed NI-C-D4

The production of rice α-amylase by tran sformed S. cerevisiae was previously shown to be dependent on stage of the cell cycle. Uchiyama et al., Biotechnol Bioeng 54:262–271,1997. The relation between mouse α-amylase production by NI-C-D4 and the cell cycle was therefore investigated. Small unbudded cells of both non-transformed and transformed,. NI-C-D4 were synchronized by arrest in $G_1$ phase of the cell cycle, released from growth arrest by transfer to fresh YPD medium, and, at vahous times thereafter, subjected to flow cytometry. Flow cytometric analysis revealed that 80 to 85% of non-transformed NI-C-D4 cells exhibited a DNA content of 1N after release from $G_1$ arrest and again 120 min later. In contrast, transformed NI-C-D4 cells exhibited a DNA content of 2N 120 min after release from $G_1$ arrest. Immunoblot analysis with antibodies to CLB2, to CDC28 (sample-loading control), or to α-amylase revealed that the amount of mouse α-amylase in cell extracts of transformed NI-C-D4 varied with the cell cycle, peaking in $G_2$-M phases and showing a periodicity similar to that of the amount of the cyclin CLB2. These results indicate that the production of heterologous α-amylase is regulated in a cell cycle-dependent manner, and that the prolonged $G_2$-M phases exhibited by transformed NI-C-D4 may contribute to the higher yield of secreted α-amylase with this strain.

OTHER EMBODIMENTS

A number of embodiments of the invention have been described. Nevertheless, it will be understood that various modifications may be made without departing from the spirit and scope of the present invention. Accordingly, other embodiments are within the scope of the following claims. For example, all protease A-deficient, pmr1-deficient, and ssa1-deficient super-secreting strains of S. cerevisiae are within the scope of this invention

What is claimed is:

1. A super-secreting protease A-deficient, PMR1 positive strain of Saccharomyces cerevisiae, wherein the strain, when starved for a nitrogen source, undergoes a pseudohyphal-like growth mode; and, when transformed with a secretion vector containing a DNA sequence which encodes a mouse α-amylase, is capable of secreting the mouse α-amylase at 2,000 to 15,000 units/liter.

2. The strain of claim 1, wherein the strain is capable of secreting the mouse α-amylase at 3,000 to 14,000 units/liter.

3. The strain of claim 2, wherein the strain is capable of secreting the mouse α-amylase at 6,000 to 13,000 units/liter.

4. The strain of claim 3, wherein the strain is capable of secreting the mouse α-amylase at 9,000 to 12,000 units/liter.

5. The strain of claim 1, wherein the strain is further characterized by reduced glycosylation of the mouse α-amylase when compared with glycosylation of α-amylase secreted by wild type strains.

6. The strain of claim 1, wherein the strain is further characterized by high stability of the vector.

7. The strain of claim 1, wherein the strain is further characterized by inability to grow at 37° C.

8. The strain of claim 1, wherein the strain is further characterized by cell cycle-dependent secretion of the mouse α-amylase.

9. The strain of claim 5, wherein the strain is further characterized by high stability of the vector.

10. The strain of claim 9, wherein the strain is further characterized by inability to grow at 37° C.

11. The strain of claim 10, wherein the strain is further characterized by a cell cycle-dependent secretion of the mouse α-amylase.

12. The strain of claim 6, wherein the strain is further characterized by inability to grow at 37° C.

13. The strain of claim 12, wherein the strain is further characterized by cell cycle-dependent secretion of the mouse α-amylase.

14. The strain of claim 7, wherein the strain is further characterized by reduced glycosylation of the mouse α-amylase when compared with glycosylation of α-amylase secreted by wild type strains.

15. The strain of claim 14, wherein the strain is further characterized by cell cycle-dependent secretion of the mouse α-amylase.

16. The strain of claim 7, wherein the strain is further characterized by cell cycle-dependent secretion of the mouse α-amylase.

17. The strain of claim 8, wherein the strain is further characterized by high stability of the vector.

18. The strain of claim 17, wherein the strain is further characterized by reduced glycosylation of the mouse α-amylase when compared with glycosylation of α-amylase secreted by wild type strains.

19. The strain of claim 8, wherein the strain is further characterized by reduced glycosylation of the mouse α-amylase when compared with glycosylation of α-amylase secreted by wild type strains.

20. The strain of claim 1, wherein the strain is NI-C-D4.

21. A supersecreting strain of *Saccharomyces cerevisiae* obtained by a process comprising:

transforming cells of a protease A-deficient and PMR1-positive *Saccharomyces cerevisiae* parent strain with a secretion vector that expresses and secretes a heterologous protein which inhibits the growth of the transformed cells;

cultivating the transformed cells in a medium containing a reduced nitrogen source and selecting a non-inhibited mutant strain, the non-inhibited mutant strain having unstable phenotypes;

maintaining cells of the unstable non-inhibited mutant strain in the stationary phase for an extended period of time and choosing a stable non-inhibited mutant strain;

growing cells of the stable non-inhibited mutant strain under conditions which favor the curing of the secretion vector;

crossing the vector-cured strain with a protease A-positive, and PMR-1 positive strain of *Saccharomyces cerevisiae* to acquire heterozygotes;

allowing the heterozygotes to sporulate to produce haploid segregants; and screening the segregants to select a strain of *Saccharomyces cerevisiae* which has a higher secretion capability than the parent strain.

\* \* \* \* \*